(12) United States Patent
Fukui et al.

(10) Patent No.: US 10,245,329 B2
(45) Date of Patent: Apr. 2, 2019

(54) COMPOSITION HAVING DYE AND CONJUGATE OF POLYETHYLENEGLYCOL AND ADDITIVE AND CONTRAST AGENT FOR PHOTOACOUSTIC IMAGING HAVING THE SAME

(71) Applicant: CANON KABUSHIKI KAISHA, Tokyo (JP)

(72) Inventors: Tatsuki Fukui, Yokohama (JP); Atsushi Takahashi, Kyoto (JP); Daisuke Sasaguri, Yokohama (JP); Kouichi Kato, Kyoto (JP); Fumiko Tomatsu, Yokohama (JP); Keigo Mizusawa, Tokyo (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 448 days.

(21) Appl. No.: 14/845,592

(22) Filed: Sep. 4, 2015

(65) Prior Publication Data
US 2016/0067359 A1 Mar. 10, 2016

(30) Foreign Application Priority Data

Sep. 8, 2014 (JP) .................. 2014-181970
Sep. 2, 2015 (JP) .................. 2015-172525

(51) Int. Cl.
*A61B 5/00* (2006.01)
*A61B 8/00* (2006.01)
(Continued)

(52) U.S. Cl.
CPC .......... *A61K 49/22* (2013.01); *A61K 49/0032* (2013.01)

(58) Field of Classification Search
None
See application file for complete search history.

(56) References Cited

U.S. PATENT DOCUMENTS 4,680,375 A * 7/1987 Elmasry ............... C09B 69/105
 428/411.1
9,138,492 B2 9/2015 Fukui et al.
(Continued)

FOREIGN PATENT DOCUMENTS

EP    2 944 326 A1   11/2015
JP    2012-520856 A   9/2012
(Continued)

OTHER PUBLICATIONS

Kasatani et al. (Chem. Lett. 1987, 1633-1636).*
(Continued)

Primary Examiner — Michael G. Hartley
Assistant Examiner — Melissa J Perreira
(74) Attorney, Agent, or Firm — Venable LLP

(57) ABSTRACT

The present invention provides contrast agents for photoacoustic imaging which exhibit high degrees of accumulation in tumor and low degrees of retention in the blood and can be administered into the blood. The contrast agents for photoacoustic imaging include a conjugate of a dye and a polyethyleneglycol represented by Formula (1), (5), (6), or (7) and an additive represented by Formula (301).

Formula (1)

Formula (5)

Formula (6)

(Continued)

Formula (7) -continued

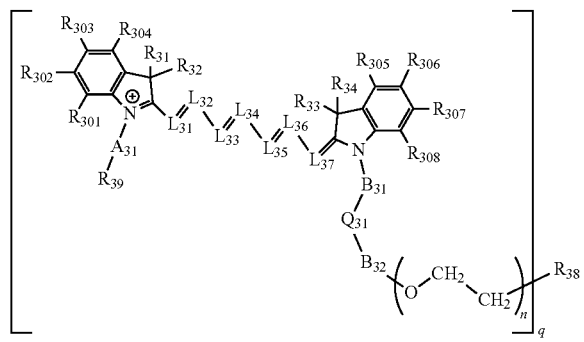

4 Claims, 1 Drawing Sheet

(51) Int. Cl.
 *A61B 10/00* (2006.01)
 *A61K 49/22* (2006.01)
 *A61K 49/00* (2006.01)

(56) References Cited

U.S. PATENT DOCUMENTS

| | | | |
|---|---|---|---|
| 2012/0114563 A1 | 5/2012 | Carter et al. | |
| 2012/0302881 A1* | 11/2012 | Teranishi | A61B 5/415 600/431 |
| 2013/0323178 A1 | 12/2013 | Yamauchi et al. | |
| 2015/0157741 A1 | 6/2015 | Yamauchi et al. | |
| 2015/0165071 A1 | 6/2015 | Takahashi et al. | |
| 2015/0290345 A1 | 10/2015 | Takahashi et al. | |
| 2015/0374856 A1 | 12/2015 | Miki et al. | |

FOREIGN PATENT DOCUMENTS

| | | | | |
|---|---|---|---|---|
| WO | WO-2009078970 A1 * | 6/2009 | ............ | C09B 11/08 |
| WO | 2010/106169 A1 | 9/2010 | | |
| WO | 2014/013730 A1 | 1/2014 | | |
| WO | 2014/129674 A1 | 8/2014 | | |

OTHER PUBLICATIONS

Guether et al. (Tett. Lett. 1997, 38, 6167-6170).*
Teresa C. Barros et al., "Polymethine Cyanine Dyes in β-Cyclodextrin Solution: Multiple Equilibria and Chemical Oxidation," 23(10) J. Phys. Org. Chem. 893-903 (Mar. 2010) (XP055139106).
Extended European Search Report in European Application No. 15002616.9 (dated Feb. 3, 2016).
Dong Ma et al., "Bioactive Supramolecular Hydrogel with Controlled Dual Drug Release Characteristics," 11(9) Biomacromolecules 2204-2212 (Jul. 2010).
Guofei Dai et al., "Progress in Pharmaceutical Applications of Cyclodextrin and its Derivatives", 14(11) Chin. J. New Drugs 1261-1264 (Dec. 2005).
First Office Action in Chinese Application No. 201510566454.X (dated Feb. 12, 2018).
Communication Pursuant to Article 94(3) EPC in European Application No. 15002616.9 (dated Jan. 25, 2019).
Second Office Action in Chinese Application No. 201510566454.X (dated Jan. 24, 2019).

* cited by examiner

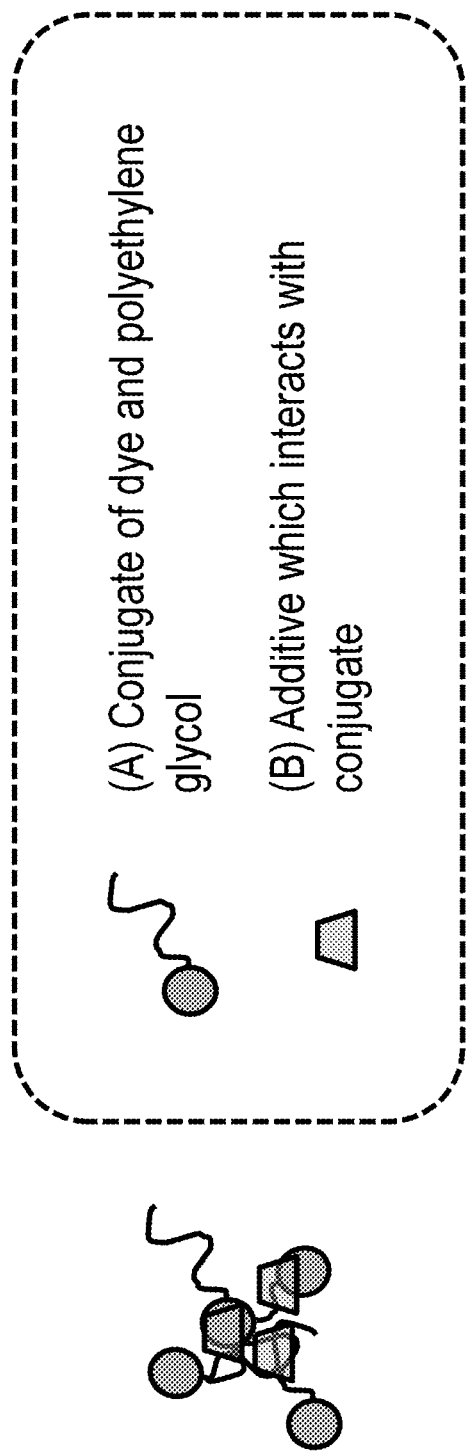

COMPOSITION HAVING DYE AND CONJUGATE OF POLYETHYLENEGLYCOL AND ADDITIVE AND CONTRAST AGENT FOR PHOTOACOUSTIC IMAGING HAVING THE SAME

BACKGROUND OF THE INVENTION

Field of the Invention

The present invention relates to compositions having a conjugate of dye and polyethyleneglycol and an additive interacting with the conjugate and contrast agents for photoacoustic imaging having such a composition.

Description of the Related Art

Photoacoustic imaging has recently gained attention as an imaging method for noninvasive diagnosis.

When a subject is irradiated with light, molecules in the subject release heat and the subject is expanded by the released heat. Photoacoustic imaging is a method for obtaining images of the subject by determining the intensity and generation position of acoustic waves generated by the volume expansion of the subject irradiated with light. In photoacoustic imaging, dye can be used as a contrast agent to increase fluorescence and the intensity of acoustic waves from the subject site.

Japanese Patent Application Laid-Open No. 2012-520856 discloses examples of use of conjugates of near-infrared dyes with synthetic polyethyleneglycol polymers having molecular weights in the range of 15 to 45 kDa as optical imaging contrast agents.

Biomacromolecules, 2010, 11(9), pp. 2204-2212 discloses examples of gels formed from mixtures of conjugates of polyethyleneglycol and heparin with cyclodextrin in which BSA (bovine serum albumin) is encapsulated.

SUMMARY OF THE INVENTION

The conjugates of near-infrared dyes with synthetic polyethyleneglycol polymers having molecular weights in the range of 15 to 45 kDa disclosed in Japanese Patent Application Laid-Open No. 2012-520856, however, exhibit high degrees of retention in the blood. Therefore, in use for photoacoustic imaging, it is difficult to distinguish photoacoustic signals of the contrast agent accumulated in tumor from those of the contrast agent remained in the blood vessel.

The mixtures of conjugates of polyethyleneglycol and heparin with cyclodextrin disclosed in Biomacromolecules, 2010, 11(9), pp. 2204-2212 are in the form of gel and difficult to be administered into the blood.

In view of the foregoing, an object of the present invention is to provide a contrast agent that exhibits a high degree of accumulation in tumor and little retention in the blood and cab be administered into the blood, by using a composition having a conjugate of dye and polyethyleneglycol and an additive interacting with the conjugate.

The present invention relates to a composition having a conjugate of dye and polyethyleneglycol and an additive interacting with the conjugate and to a contrast agent for photoacoustic imaging having the composition.

Contrast agents according to the present invention provide excellent visualization of tumor because they include a conjugate of dye and polyethyleneglycol and an additive interacting with the conjugate and thereby exhibit high degrees of accumulation in tumor and little retention in the blood.

Further features of the present invention will become apparent from the following description of exemplary embodiments with reference to the attached drawing.

BRIEF DESCRIPTION OF THE DRAWINGS

FIGURE illustrates a configuration of a composition according to an embodiment of the present invention.

DESCRIPTION OF THE EMBODIMENTS

Preferred embodiments of the present invention will now be described in detail in accordance with the accompanying drawing.

Embodiments of the present invention will now be described, but the present invention is not limited to the embodiments.

(Configuration of Embodiment)

Compositions according to this embodiment has (A) a conjugate of dye and polyethyleneglycol and (B) an additive interacting with the conjugate as illustrated in FIGURE.

After the administration into the blood, aggregates of (A) and (B) move to tumor from the blood. Meanwhile, aggregates remaining in the blood are degraded and eliminated from the body.

Therefore, the compositions according to this embodiment provide excellent visualization of tumor because they exhibit high degrees of accumulation in tumor and little retention in the blood.

(Conjugate of Dye and Polyethyleneglycol)

A conjugate of dye and polyethyleneglycol according to the present invention has an absorption band at a wavelength in the rage of 600 nm to 1300 nm. The phrase "has an absorption band" means that the conjugate has a molar extinction coefficient of $10^6$ $M^{-1}$ $cm^{-1}$ at a wavelength in the range of 600 nm to 1300 nm. The term "polyethyleneglycol," as used herein, includes polyethyleneglycol derivatives, such as those having a structure in which polyethyleneglycol is partially substituted.

In this embodiment, the structures of the conjugates of dye and polyethyleneglycol are represented by Formula (1), (5), (6), (7).

Formula (1)

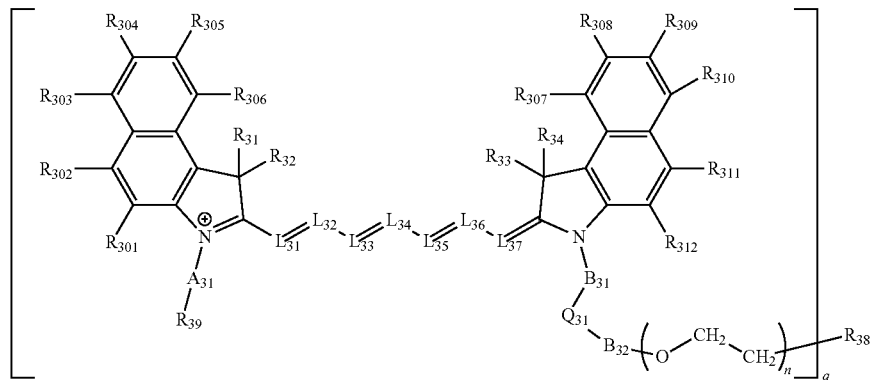

Formula (5)

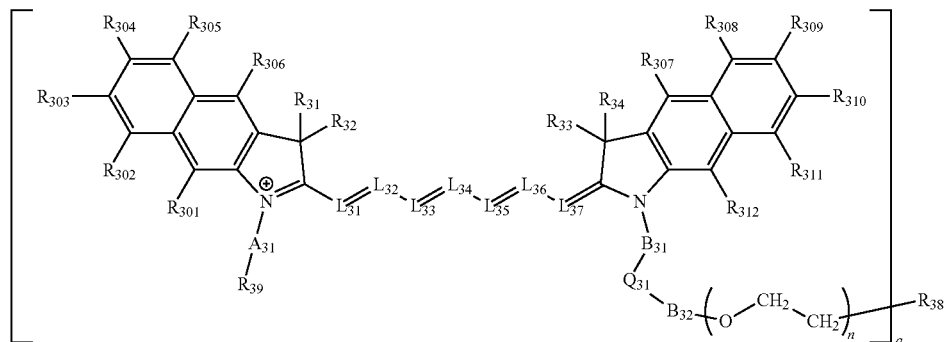

Formula (6)

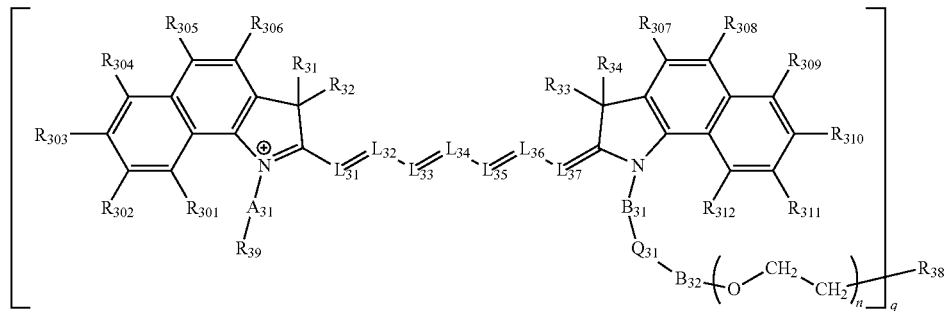

Formula (7)

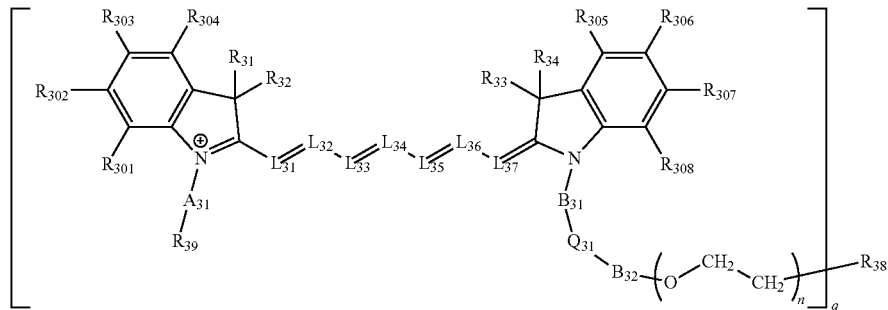

In Formulas (1), (5), (6) and (7) above, $R_{301}$ to $R_{312}$ are each independently selected from the group consisting of a hydrogen atom, a halogen atom, $-PO_3T_{301}$, a substituted or unsubstituted phenyl group, thiophene group, or pyridinyl group and a linear or branched alkyl group having 1 to 18 carbon atoms; $T_{301}$ is selected from the group consisting of a hydrogen atom, a sodium atom and a potassium atom; $R_{31}$ to $R_{34}$ are each independently selected from the group consisting of a hydrogen atom and a linear or branched alkyl group having 1 to 18 carbon atoms; $A_{31}$, $B_{31}$ and $B_{32}$ each independently represent a linear or branched alkylene group having 1 to 18 carbon atoms; $L_{31}$ to $L_{37}$ are each independently selected from the group consisting of CH and $CR_{35}$ and may form a 4- to 6-membered ring; $R_{35}$ is selected from the group consisting of a linear or branched alkyl group having 1 to 18 carbon atoms, a halogen atom, a substituted or unsubstituted phenyl group, pyridinyl group, or benzyl group, $ST_{302}$ and a linear or branched alkylene group having 1 to 18 carbon atoms; $T_{302}$ is selected from the group consisting of a linear or branched alkyl group having 1 to 18 carbon atoms, a substituted or unsubstituted phenyl group and a linear or branched alkylene group having 1 to 18 carbon atoms; $Q_{31}$ is selected from the group consisting of —$CONT_{31}$—, —$NT_{31}CO$—, —$NT_{31}(C=O)NT_{31}$—, —$NT_{31}(C=S)NT_{31}$—, —$NT_{31}(C=O)O$—, —O—, —S—, —$S(=O)_2NT_{31}$—, —$OP(=O)(OT_{31})O$—, —S—S—, —$CT_{31}=N$—, —$CT_{31}=N$—NH—, —$CT_{31}=N$—O—, —$CT_{31}=N$—NH—O—, —$CONT_{31}$-$R_{37}$—(C=O)O—, —$CONT_{31}$—$R_{37}$—$CONT_{31}$- and Formulas (2) and (3); $T_{31}$ is selected from the group consisting of a hydrogen atom and an alkyl group having 1 to 5 carbon atoms; $R_{37}$ is selected from the group consisting of —$CH(CO_2T_{37})$-, —$CH(CH_2CO_2T_{37})$- and a linear or branched alkylene group having 1 to 18 carbon atoms; $T_{37}$ is selected from the group consisting of a hydrogen atom, a sodium atom, a potassium atom and an alkyl group having 1 to 5 carbon atoms; $R_{38}$ is selected from the group consisting of an alkyl group having 1 to 18 carbon atoms, a hydrogen atom, —$OCH_3$, —$NH_2$, —OH, —$CO_2T_{38}$, —$S(=O)_2OT_{38}$, —$P(=O)(OT_{38})_2$ and —$OP(=O)(OT_{38})_2$; $T_{38}$ is selected from the group consisting of a hydrogen atom, a sodium atom and a potassium atom; $R_{39}$ is selected from the group consisting of a hydrogen atom, —$OCH_3$, —$NH_2$, —OH, —$S(=O)_2OT_{39}$, —$CO_2T_{39}$, —$P(=O)(OT_{39})_2$, —$CONH$—$CH(CO_2T_{39})$—$CH_2C(=O)OT_{39}$, —$CONH$—$CH(CO_2T_{39})$—$CH_2CH_2(C=O)OT_{39}$ and —$OP(=O)(OT_{39})_2$; $T_{39}$ is selected from the group consisting of a hydrogen atom, a sodium atom and a potassium atom;

q is an integer from 1 to 20;

n is an integer from 1 to 2500.

Formula (2)

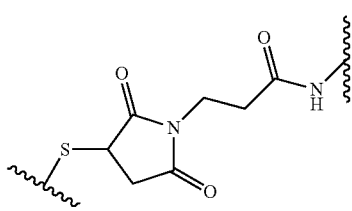

Formula (3)

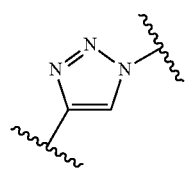

In Formulas (1), (5), (6) and (7) above, n is preferably equal to or more than 2 and equal to or less than 500, preferably equal to or more than 2 and equal to or less than 250, and more preferably equal to or more than 20 and equal to or less than 250.

In Formulas (1), (5), (6) and (7) above, q is preferably equal to or more than 1 and equal to or less than 10, and more preferably equal to or more than 1 and equal to or less than 4.

Examples of compounds represented by Formula (1) include those represented by Formula (501) and (601).

Formula (501)

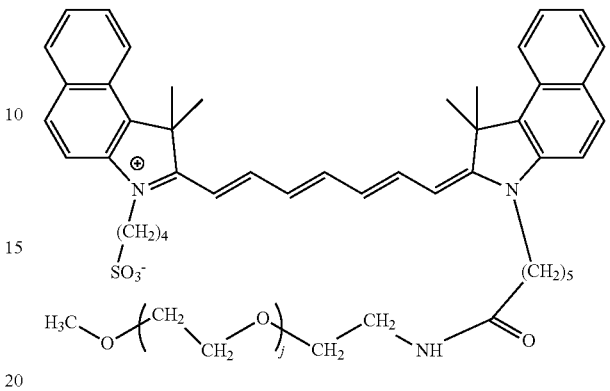

Formula (601)

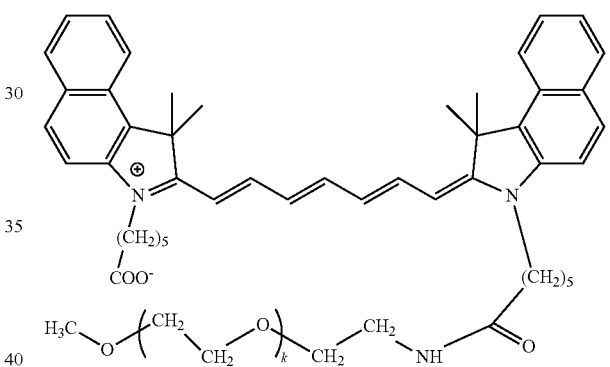

In Formulas (501) and (601), j and k are each an integer from 1 to 2500.

(Dye)

A dye in the aforementioned conjugate of dye and polyethyleneglycol has a structure having a methine chain and 5-membered rings containing N bound to the both ends of the methine chain as a basic structure.

The dye in this embodiment can be a compound that can absorb light at a wavelength in the range of 600 nm to 1300 nm. The dye in this embodiment can have a molar extinction coefficient equal to or more than $10^6$ $M^{-1}$ $cm^{-1}$. The polyethyleneglycol moiety exhibit little absorption at wavelengths in the aforementioned range. Therefore, in other words, the polymer according to this embodiment can have a molar extinction coefficient of equal to or more than $10^6$ $M^{-1}$ $cm^{-1}$ at a wavelength in the range of 600 nm to 1300 nm.

Examples of the dye in this embodiment include compounds represented by Formulas (11), (15), (16) and (17) below.

Formula (11)

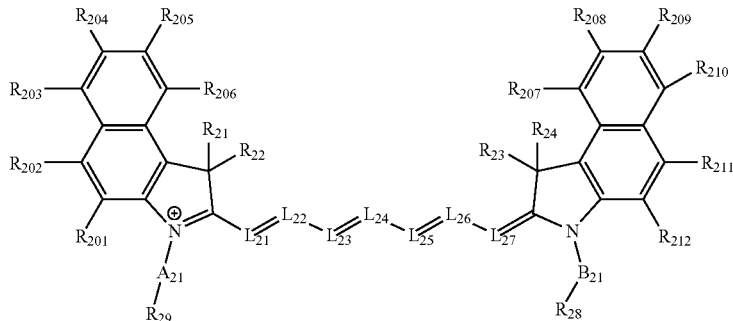

Formula (15)

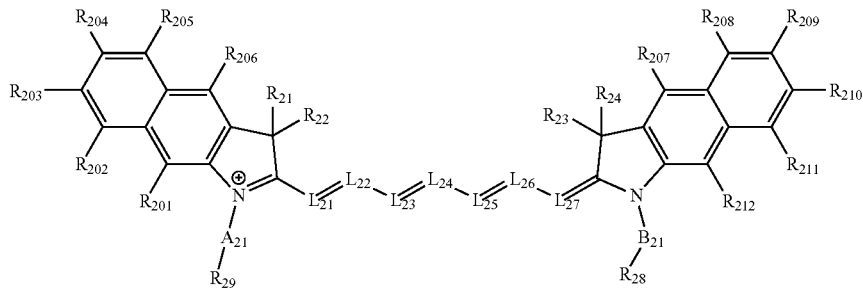

Formula (16)

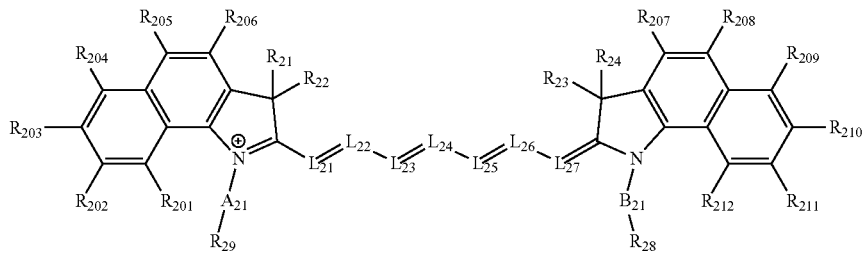

Formula (17)

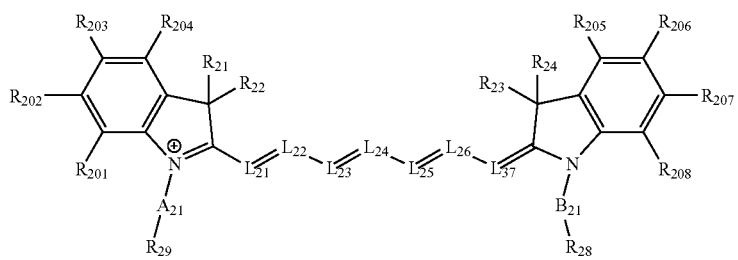

In Formulas (11), (15), (16) and (17) above, $R_{201}$ to $R_{212}$ are each independently selected from the group consisting of a hydrogen atom, a halogen atom, $-PO_3T_{201}$, a benzene ring, a thiophene ring, a pyridine ring and a linear or branched alkyl group having 1 to 18 carbon atoms; $T_{201}$ is selected from the group consisting of a hydrogen atom, a sodium atom and a potassium atom; $R_{21}$ to $R_{24}$ are each independently selected from the group consisting of a hydrogen atom and a linear or branched alkyl group having 1 to 18 carbon atoms; $A_{21}$ and $B_{21}$ each independently represent a linear or branched alkylene group having 1 to 18 carbon atoms; $L_{21}$ to $L_{27}$ are each independently selected from the group consisting of CH and $CR_{25}$ and may form a 4- to 6-membered ring; $R_{25}$ is selected from the group consisting of a linear or branched alkyl group having 1 to 18 carbon atoms, a halogen atom, a benzene ring, a pyridine ring, a benzyl group, $ST_{202}$ and a linear or branched alkylene group having 1 to 18 carbon atoms; $T_{202}$ is selected from the group consisting of a linear or branched alkyl group having 1 to 18 carbon atom, a substituted or unsubstituted phenyl group and a linear or branched alkylene group having 1 to 18 carbon atoms; $R_{28}$ is selected from the group consisting of a hydrogen atom, $-OCH_3$, $-NH_2$, $-OH$, $-CO_2T_{28}$, $-S(=O)_2OT_{28}$, $-P(=O)(OT_{28})_2$, $-CONH-CH(CO_2T_{28})-CH_2(C=O)OT_{28}$, $-CONH-CH(CO_2T_{28})-CH_2CH_2(C=O)OT_{28}$ and $-OP(=O)(OT_{28})_2$; $T_{28}$ is selected from the group consisting of a hydrogen atom, a sodium atom and a potassium atom; $R_{29}$ is selected from the group consisting of a hydrogen atom, $-OCH_3$, $-NH_2$, $-OH$, $-CO_2T_{29}$, $-S(=O)_2OT_{29}$, $-P(=O)(OT_{29})_2$, $-CONH-CH(CO_2T_{29})-CH_2(C=O)OT_{29}$, $-CONH-CH(CO_2T_{29})-CH_2CH_2(C=O)OT_{29}$ and $-OP(=O)(OT_{29})_2$;

$T_{29}$ is selected from the group consisting of a hydrogen atom, a sodium atom and a potassium atom.

The compounds represented by Formulas (11), (15), (16) and (17) above can be compounds represented by Formulas (101) and (102) (which may be hereinafter abbreviated as Compounds (101) and (102)).

Formula (101)

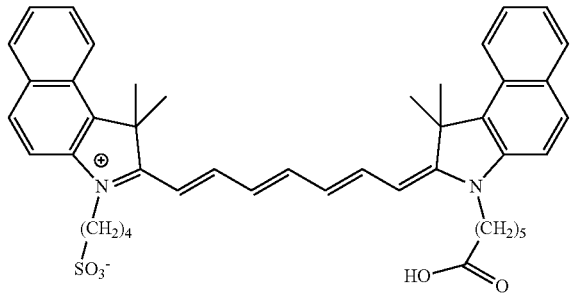

Formula (102)

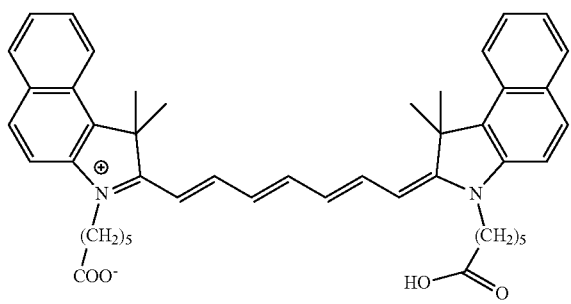

(Polyethyleneglycol)

The polyethyleneglycol in the aforementioned conjugate of dye and polyethyleneglycol can have molecular weights equal to or more than 100 to have high dispersibility, and equal to or less than 100000 to avoid making the viscosity of the solution too high.

The conjugate of dye and polyethyleneglycol according to this embodiment may have branched as well as linear structures.

The polyethyleneglycol may have plural amino groups which can be bound to the dye. This allows binding of a plurality of dye molecules, which increases the number of bound dye molecules per unit amount of polyethyleneglycol.

Examples of the polyethyleneglycol according to this embodiment include compounds represented by Formula (201).

Formula (201)

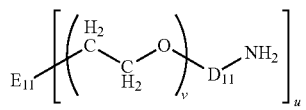

In Formula (201) above, $D_{11}$ represents a linear or branched alkylene group having 1 to 18 carbon atoms; $E_{11}$ is selected from the group consisting of a linear or branched alkyl group having 1 to 18 carbon atoms, a hydrogen atom, —$OCH_3$, —$NH_2$, —OH, —$CO_2T_{38}$, —$S(=O)_2OT_{38}$, —$OP(=O)(OT_{38})_2$ and —$OP(=O)(OT_{38})_2$;
u is an integer from 1 to 20;
v is an integer from 1 to 2500.

The compounds represented by Formula (201) above can be compounds represented by Formula (202) below (which may be hereinafter abbreviated as Compound (202)).

Formula (202)

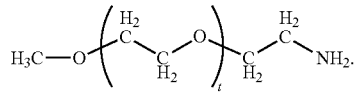

In Formula (202) above, t is an integer from 1 to 2500.
In Formula (202) above, the molecular weight is preferably 1000 to 40000, preferably 2000 to 30000, and more preferably 5000 to 10000.

Other examples include SUNBRIGHT ®PA Series (NOF Corporation) <SUNBRIGHT MEPA-20H, SUNBRIGHT MEPA-50H, SUNBRIGHT MEPA-12T, SUNBRIGHT MEPA-20T, SUNBRIGHT MEPA-30T, SUNBRIGHT MEPA-40T>, SUNBRIGHT ® EA Series (NOF Corporation) <SUNBRIGHT ME-050EA, SUNBRIGHT ME-100EA, SUNBRIGHT ME-200EA (a compound having a molecular weight of 20000 represented by Formula (202)), SUNBRIGHT ME-300EA, SUNBRIGHT ME-400EA>, Methoxy PEG amine (NANOCS) <PG1-AM-350, PG1-AM-550, PG1-AM-750, PG1-AM-1k, PG1-AM-2k, PG1-AM-5k>, SUNBRIGHT GL2-200PA (NOF Corporation), SUNBRIGHT GL2-400PA (NOF Corporation), SUNBRIGHT GL2-600PA (NOF Corporation), SUNBRIGHT GL3-400PA100U (NOF Corporation), SUNBRIGHT GL4-600PA (NOF Corporation), SUNBRIGHT GL4-800PA (NOF Corporation), SUNBRIGHT PTE2-400EA (NOF Corporation), SUNBRIGHT PTE-400PA (NOF Corporation, a compound having a molecular weight of 40000 represented by Formula (204) below), SUNBRIGHT PTE-200PA (NOF Corporation, a compound having a molecular weight of 20000 represented by Formula (204) below), SUNBRIGHT HGEO-150PA (NOF Corporation), SUNBRIGHT HGEO-400PA (NOF Corporation), SUNBRIGHT PTE2-200MA2 (NOF Corporation) and SUNBRIGHT PTE-400MA2 (NOF Corporation).

Formula (204)

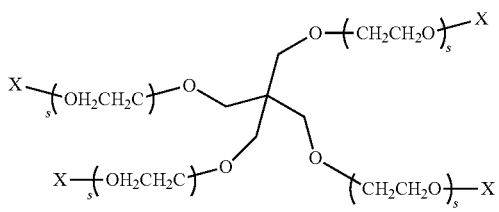

In Formula (204) above, each s is independently an integer from 1 to 2500. In Formula (204) above, the molecular weight can be equal to or more than 20000 and equal to or less than 60000.
In Formula (204) above, X is $(CH_2)_3$—$NH_2$.

(Conjugation Process of Dye and Polyethyleneglycol)

The conjugation process of dye and polyethyleneglycol according to this embodiment is not particularly limited as for the reaction thereof, as long as a conjugate of a dye represented by Formula (11), (15), (16) or (17) above and a compound having polyethyleneglycol represented by Formula (201) above can be obtained.

Examples of the reaction for conjugating dye and polyethyleneglycol include the following. For example, any of a method of using a condensing agent for reacting carboxyl groups and amino groups, a method of salt formation and condensation by dehydration, a method of using a dehydrating agent, and a method of converting carboxyl groups into acid chlorides and reacting them with amino groups can be used.

Available examples of the condensing agent include carbodiimide condensing agents and phosphorus condensing agents.

Examples of the carbodiimide condensing agents include N,N'-dicyclohexylcarbodiimide (DCC) and water-soluble carbodiimide (WSC).

The amount of the condensing agent to be used is in the range of equal to or more than 0.1 fold, preferably equal to or more than 1 fold in molar ratio to the compound represented by Formula (11), (15), (16), or (17). The condensing agent itself can be used as a reaction solvent.

The amount of the compound represented by Formula (11), (15), (16), or (17) above to be used in the reaction process in this embodiment is preferably in the range of 0.1 to 50.0 fold, more preferably in the range of 1.0 to 20.0 fold, and particularly preferably in the range of 1.0 to 10.0 fold in molar ratio to the number of the amino group contained in the compound represented by Formula (201). This is because reducing the amount of the compound represented by Formula (11), (15), (16), or (17) used in the reaction process reduces the burden of removing the unreacted compound represented by Formula (11), (15), (16), or (17) from samples in the purification process.

(Organic Solvent Used in Reaction Process)

The organic solvent to be used in the reaction process in this embodiment is not particularly limited, as long as the compound represented by Formula (11), (15), (16), or (17) above can be conjugated with the compound represented by Formula (201) above.

Examples of the organic solvent to be uses in the reaction process include hydrocarbons such as hexane, cyclohexane and heptane; ketones such as acetone and methylethylketone; ethers such as dimethylether, diethylether and tetrahydrofuran; halogenated hydrocarbons such as dichloromethane, chloroform, carbontetrachloride, dichloroethane and trichloroethane; aromatic hydrocarbons such as benzene and toluene; aprotic polar solvents such as N,N-dimethylformamide (which may be hereinafter abbreviated as DMF) and dimethylsulfoxide (DMSO); and pyridine derivatives. Mixtures of two or more of these organic solvents can be also used.

Preferable examples include aprotic polar solvents such as DMF and dimethylsulfoxide; and halogenated hydrocarbons such as dichloromethane and chloroform. This is because the compounds represented by Formulas (11), (15), (16) and (17) above are highly soluble in these organic solvents and such a compound can react in a sufficiently dispersed state. The amount of the organic solvent to be used in the reaction process can be determined depending on the reaction conditions as appropriate.

In the reaction process in this embodiment, the reaction temperature is not particularly limited, but it is usually in the range of equal to or higher than 0° C. and equal to or lower than the boiling point of the solvent. It is however desirable to react at the temperature most suitable to the condensing agent to be used.

In the reaction process in this embodiment, the reaction time is, for example, in the range of 1 to 48 hours.

(Purification Process)

The purification process in this embodiment is not particularly limited as for the method therefore as long as a conjugate of a dye represented by Formula (11), (15), (16), or (17) above and a compound having polyethyleneglycol represented by Formula (201) above can be purified.

Examples of the method for isolating and purifying the conjugate obtained in the aforementioned reaction process include normal phase chromatography, size exclusion chromatography, ultrafiltration and dialysis using organic solvents.

(Organic Solvents to Be Used in Purification Process)

Examples of the organic solvents to be used in the purification process in this embodiment include hydrocarbons such as hexane, cyclohexane and heptane; ketones such as acetone and methylethylketone; ethers such as dimethylether, diethylether and tetrahydrofuran; halogenated hydrocarbons such as dichloromethane, chloroform, carbontetrachloride, dichloroethane and trichloroethane; aromatic hydrocarbons such as benzene and toluene; aprotic polar solvents such as N,N-dimethylformamide and dimethylsulfoxide; pyridine derivatives; and alcohols such as methanol and ethanol. Mixtures of two or more of these solvents can be also used.

Preferable examples include halogenated hydrocarbons such as dichloromethane and chloroform; and alcohols such as methanol and ethanol. This is because the dyes represented by Formulas (11), (15), (16) and (17) above and the aforementioned conjugates are highly soluble in these solvents and such a dye and a conjugate can be purified in sufficiently dispersed states.

The organic solvent to be used in the purification process in this embodiment and the organic solvent to be used in the aforementioned reaction process can be the same.

(Additive)

Examples of the additive in this embodiment include compounds represented by Formula (301).

Formula (301)

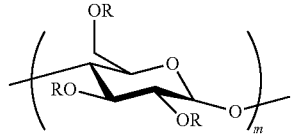

Formula (401)

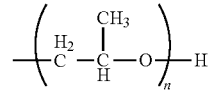

In Formula (301) above, m is an integer selected from 1 to 20; Rs are each independently a structure represented by Formula (401) above or a hydrogen atom.

In Formula (401) above, n is an integer selected from 1 to 20.

Examples of the additive include α-cyclodextrin (Formula (302)), β-cyclodextrin (Formula (303)), hydroxypropyl-β-cyclodextrin (Formula (304)) and γ-cyclodextrin (Formula (305)). At least one of these additives can be used and plural of these additives may be used.

Formula (302)

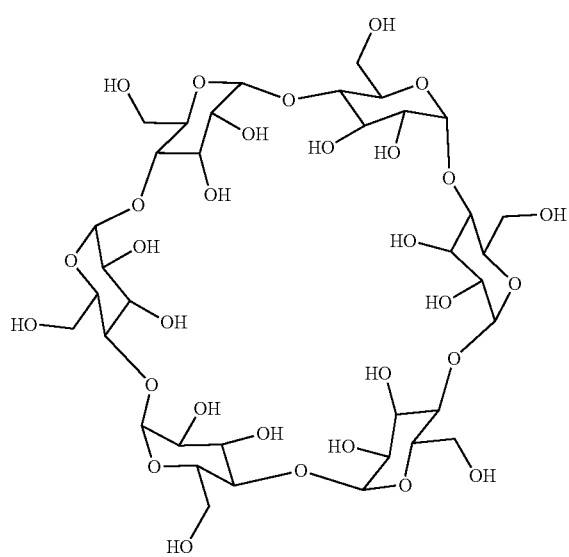

Formula (303)

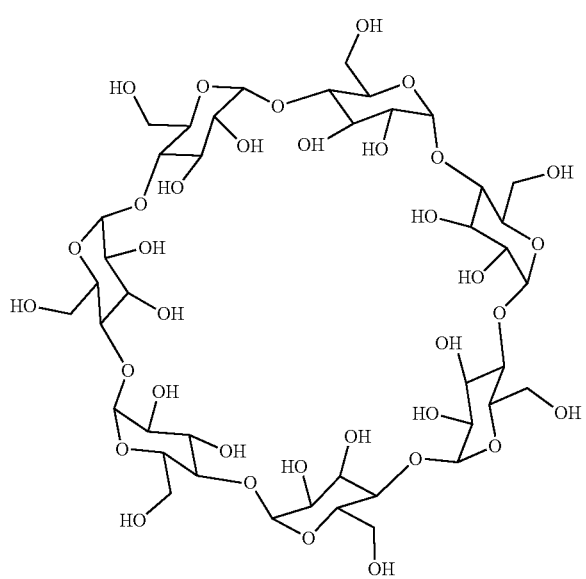

Formula (304)

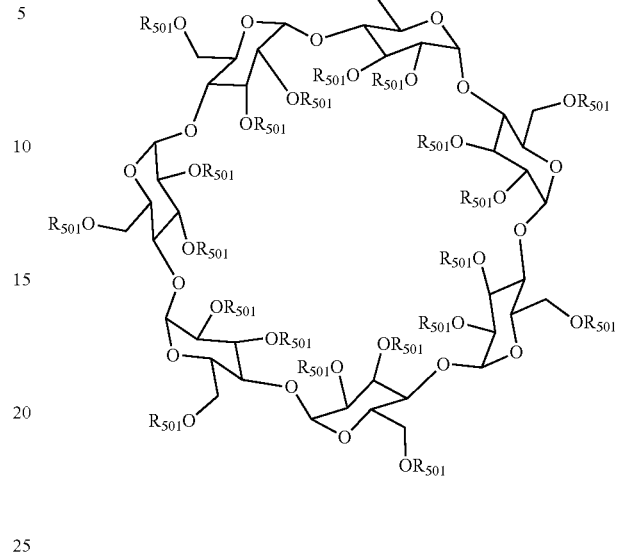

Formula (305)

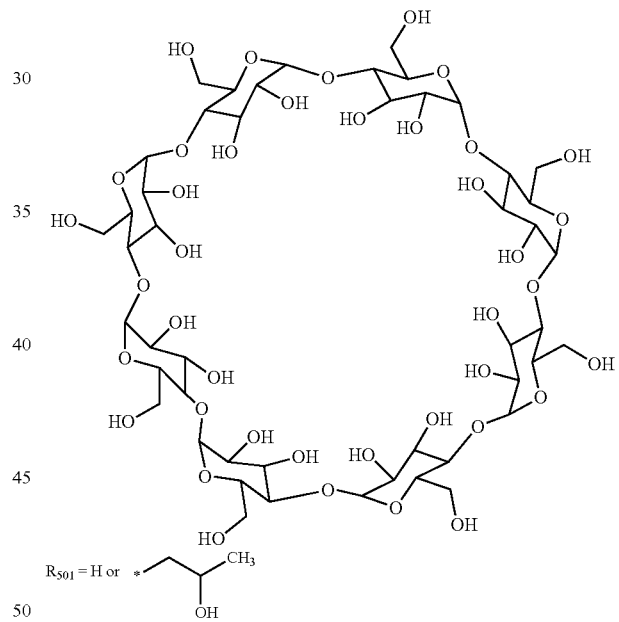

$R_{501}$ = H or (Contrast Agent for Photoacoustic Imaging)

In this embodiment, a contrast agent for photoacoustic imaging has the aforementioned composition and a dispersion medium. Examples of the dispersion medium include physiological saline, distilled water for injection, phosphate-buffered saline and aqueous solutions of glucose.

(Method for Preparing Composition)

A method for producing the composition according to this embodiment includes conjugating a polyethylene glycol represented by Formula (201) below and a dye represented by Formula (11), (15), (16), or (17) below to obtain a conjugate. The method further includes mixing the obtained conjugate with an additive represented by Formula (301) below.

Formula (201)

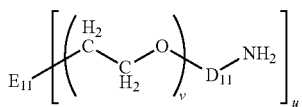

In Formula (201) above, $D_{11}$ represents a linear or branched alkylene group having 1 to 18 carbon atoms;
$E_{11}$ is selected from the group consisting of a linear or branched alkyl group having 1 to 18 carbon atoms, a hydrogen atom, —$OCH_3$, —$NH_2$, —OH, —$CO_2T_{38}$, —$S(=O)_2OT_{38}$, —$P(=O)(OT_{38})_2$ and —$OP(=O)(OT_{38})_2$;
u is an integer from 1 to 20;
v is an integer from 1 to 2500.

In Formulas (11), (15), (16) and (17), $R_{201}$ to $R_{212}$ are each independently selected from the group consisting of a hydrogen atom, a halogen atom, —$PO_3T_{201}$, a benzene ring, a thiophene ring, a pyridine ring and a linear or branched alkyl group having 1 to 18 carbon atoms; $T_{201}$ is selected from the group consisting of a hydrogen atom, a sodium atom and a potassium atom; $R_{21}$ to $R_{24}$ are each independently selected from the group consisting of a hydrogen atom and a linear or branched alkyl group having 1 to 18 carbon atoms; $A_{21}$ and $B_{21}$ each independently represent a linear or branched alkylene group having 1 to 18 carbon atoms; $L_{21}$ to $L_{27}$ are each independently selected from the group consisting of CH and $CR_{25}$ and may form a 4- to 6-membered ring; $R_{25}$ is selected from the group consisting of a linear or branched alkyl group having 1 to 18 carbon atoms, a halogen atom, a benzene ring, a pyridine ring, a benzyl group, $ST_{202}$ and a Formula (11)

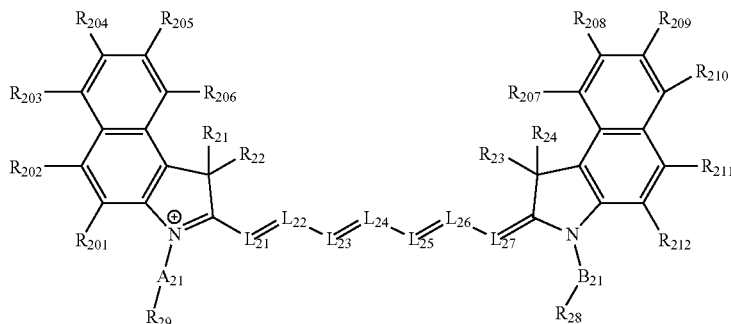

Formula (15)

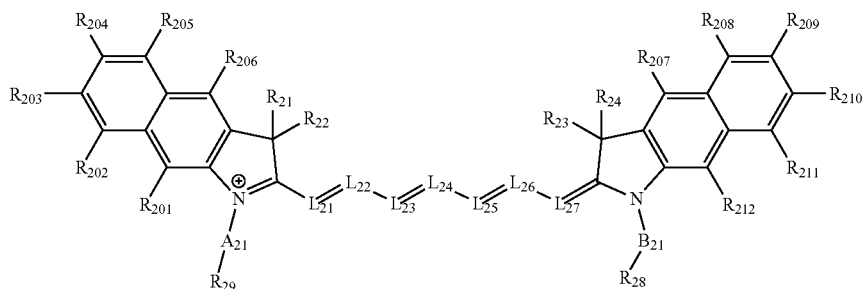

Formula (16)

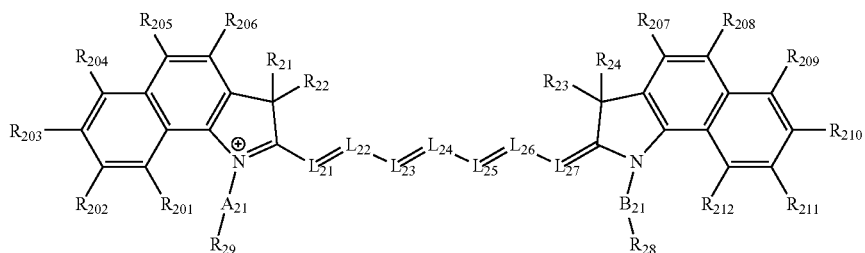

Formula (17)

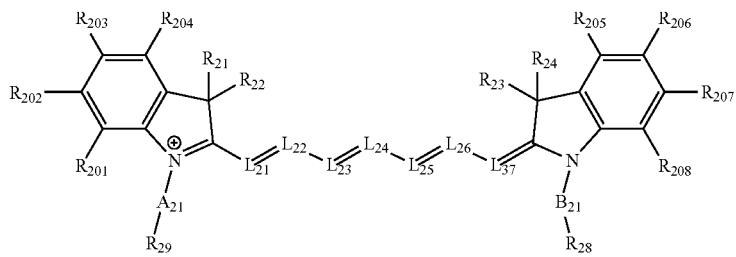

linear or branched alkylene group having 1 to 18 carbon atoms; $T_{202}$ is selected from the group consisting of a linear or branched alkyl group having 1 to 18 carbon atom, a substituted or unsubstituted phenyl group and a linear or branched alkylene group having 1 to 18 carbon atoms; $R_{28}$ is selected from the group consisting of a hydrogen atom, —$OCH_3$, —$NH_2$, —OH, —$CO_2T_{28}$, —S(=O)$_2OT_{28}$, —P(=O)($OT_{28}$)$_2$, —CONH—CH($CO_2T_{28}$)-$CH_2$(C=O)$OT_{28}$, —CONH—CH($CO_2T_{28}$)-$CH_2CH_2$(C=O)$OT_{28}$ and —OP(=O)($OT_{28}$)$_2$; $T_{28}$ is selected from the group consisting of a hydrogen atom, a sodium atom and a potassium atom; $R_{29}$ is selected from the group consisting of a hydrogen atom, —$OCH_3$, —$NH_2$, —OH, —$CO_2T_{29}$, —S(=O)$_2OT_{29}$, —P(=O)($OT_{29}$)$_2$, —CONH—CH($CO_2T_{29}$)-$CH_2$(C=O)$OT_{29}$, —CONH—CH($CO_2T_{29}$)-$CH_2CH_2$(C=O)$OT_{29}$ and —OP(=O) ($OT_{29}$)$_2$; $T_{29}$ is selected from the group consisting of a hydrogen atom, a sodium atom and a potassium atom;

Formula (301)

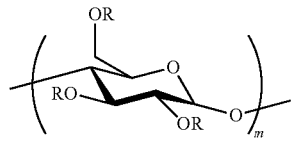

Formula (401)

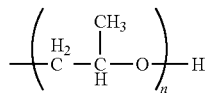

In Formula (301) above, m is an integer selected from 1 to 20; Rs are each independently a structure represented by Formula (401) or a hydrogen atom.
In Formula (401) above, n is an integer selected from 1 to 20.

In the method for production according to this embodiment, polyethyleneglycol can be a compound represented by Formula (202) below.

Formula (202)

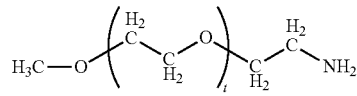

In Formula (202) above, t is an integer from 1 to 2500.
In Formula (202) above, the molecular weight is preferably 1000 to 40000 and more preferably 5000 to 10000.

The additive can be at least one of α-cyclodextrin, β-cyclodextrin, hydroxypropyl-β-cyclodextrin and γ-cyclodextrin.

The contrast agent for photoacoustic imaging may be produced by mixing the aforementioned composition and a dispersion medium.

The method for producing the composition according to this embodiment will now be described in detail. The method for preparing the composition according to this embodiment can employ a known method. Examples of such method include nanoemulsion, nanoprecipitation and mixing and stirring with a good solvent.

Examples of solvents to be used in the method for preparation include hydrocarbons such as hexane, cyclohexane and heptane; ketones such as acetone and methylethylketone; ethers such as diethylether and tetrahydrofuran; halogenated hydrocarbons such as dichloromethane, chloroform, carbontetrachloride, dichloroethane and trichloroethane; aromatic hydrocarbons such as benzene and toluene; esters such as ethyl acetate and butyl acetate; aprotic polar solvents such as N,N-dimethylformamide and dimethylsulfoxide; water; and pyridine derivatives. These solvents may be used alone or in any mixture thereof.

In nanoemulsion, emulsions can be prepared by an emulsification method conventionally known. Examples of the method known conventionally include intermittent shaking, stirring using a mixer such as a propeller type stirrer and a turbine type stirrer, colloidal milling, homogenizing and ultrasonic irradiation. These methods can be used alone or in combination thereof. The emulsion may be prepared in single-step or in multi-step emulsification. The method of emulsification is not limited to these methods as long as the method can achieve the purpose of the present invention.

In nanoprecipitation, the composition of this embodiment can be prepared by a method of admixing an organic solvent to be dispersed to an aqueous solution and stirring the mixture or a method of admixing an aqueous solution to an organic solvent to be dispersed and stirring the mixture.

In nanoemulsion or nanoprecipitation, the conjugate of dye and polyethylene glycol and the additive can be dissolved into either of an aqueous solution or an organic solvent to be dispersed.

In mixing and stirring with a good solvent, the composition of this embodiment can be prepared by mixing and stirring (1) a solution of the conjugate of dye and polyethylene glycol in a good solvent and (2) a solution of the additive in a good solvent.

(Mixing Ratio of Organic Solvent to be Dispersed and Aqueous Solution)

The weight ratio of the aqueous solution and the organic solvent to be used in nanoemulsion is not particularly limited as long as an oil in water (O/W) emulsion can be formed. However, the weight ratio of the aqueous solution and the organic solvent can be in the range of 2:1 to 1000:1.

In nanoprecipitation, the weight ratio of the aqueous solution and the organic solvent to be used is not particularly limited as long as the composition of this embodiment can be obtained. However, the weight ratio of the aqueous solution and the organic solvent can be in the range of 1:1 to 1000:1.

In mixing and stirring with a good solvent, the weight ratio of the good solvent solutions (1) and (2) to be used is not particularly limited as long as the composition of this embodiment can be obtained. However, the weight ratio of the good solvent solutions (2) and (1) to be used can be in the range of 1:1 to 1000:1.

(Concentrations of Conjugate of Dye and Polyethyleneglycol and Additive in Solution)

The concentrations of the conjugate of dye and polyethyleneglycol in respective solutions are not particularly limited as long as the conjugate is dissolved. However, the concentrations can be 0.0005 to 300 mg/ml. The concentrations of the additive in respective solutions are not particularly limited as long as the additive is dissolved. However, the concentrations can be 0.0005 to 300 mg/ml.

(Distillation of Organic Solvent)

The organic solvent can be distilled off from the prepared composition, as needed.

The distillation can be performed by any method conventionally known and examples of such method include evaporation by heating and methods using a pressure reducing apparatus such as an evaporator.

The distillation is not limited to the aforementioned methods as long as the purpose of the present invention can be achieved.

(Purification of Composition)

The purification of the composition produced in this embodiment can be performed by any method conventionally known. Examples of such method include size exclusion chromatography, ultrafiltration, dialysis and centrifugation.

The method of purification is not limited to the aforementioned methods as long as the purpose of the present invention can be achieved.

(Photoacoustic Imaging)

In one embodiment of the invention, the composition according to the present invention can be used as a contrast agent for photoacoustic imaging. As used herein, the term "photoacoustic imaging" includes photoacoustic tomography. The photoacoustic imaging using the contrast agent according to this embodiment includes administering the contrast agent according to this embodiment to a subject or a sample obtained from the subject and irradiating the subject or the sample obtained from the subject with pulsed light. The photoacoustic imaging further includes measuring photoacoustic signals from a signal source substance in the subject or the sample obtained from the subject.

The following is an example of the photoacoustic imaging using the contrast agent for acoustic imaging according to this embodiment. The contrast agent for acoustic imaging according to this embodiment is administered to a subject or added to a sample such as an organ obtained from the subject. The aforementioned subject refers to any of living organisms including, but not limited to, human, laboratory animals and pets. Examples of the aforementioned sample in the subject or obtained from the subject include organs, tissues, tissue sections, cells and cell lysates. After the administration or addition of the agent, the subject was irradiated with pulsed laser light in the infrared wavelength region.

In the photoacoustic imaging according to this embodiment, the wavelength of light to be applied can be selected according to the laser light source to be used. In the photoacoustic imaging according to this embodiment, the subject can be irradiates with light at a wavelength in the near infrared region of 600 nm to 1300 nm, which is referred to as "window of biological tissue" because of less effects of absorption and diffusion of light in living tissues, to acquire acoustic signals efficiently.

Photoacoustic signals (acoustic wave) from the contrast agent according to this embodiment are detected with an acoustic wave detector, for example, a piezoelectric transducer, and converted into electrical signals. Based on the electrical signals obtained with the acoustic wave detector, the position and size of the absorber in the subject or the like or the distribution of optical property values such as molar extinction coefficient can be calculated. For example, if the contrast agent is detected at or beyond a threshold, the signal source substance is presumed to be contained in the subject or the sample obtained from the subject.

In the present invention, the leak of dye is suppressed and this causes quenching due to the accumulation of dye to prevent energy transfer from applied pulsed light into fluorescence, allowing conversion into more thermal energy. Therefore acoustic signals can be acquired more effectively.

EXAMPLES

The present invention will now be described along with Examples to describe features of the present invention more clearly. The present invention is however not limited to these Examples and materials, composition conditions, and reaction conditions can be changed as long as a composition having equivalent functions and effects is obtained.

(Method of Evaluating Photoacoustic Properties)

Photoacoustic signals are measured by irradiating a sample with pulsed laser light, detecting photoacoustic signals from the sample with a piezoelectric element, amplifying the signals with a high speed preamplifier, and then measuring with a digital oscilloscope. The concrete conditions are as follows. A titanium sapphire laser (Lotis) was used as a light source. The following conditions were used: wavelengths of 750 nm and 780 nm, an energy density of 12 mJ/cm$^2$, a pulse width of 20 nanoseconds, and a pulse repetition frequency of 10 Hz. The ultrasonic transducer, model V303 (Panametrics-NDT) was used. The following conditions were used: a center frequency of 1 MHz, an element size of 0.5, a measurement distance of 25 mm (Non-focus), an amplifier of +30 dB (ultrasonic preamplifier, Model 5682, Olympus). A polystyrene cuvette with a light path length of 0.1 cm and a sample volume of about 200 μl was used as a measurement container. Trigger/photoacoustic light was detected with photodiode using the measuring instrument DPO4104 (Tektronix) and measured as averages of 128 data acquisition (128 pulses).

Example A1

105.7 mg of PEG having an amino group (NOF Corporation, SUNBRIGHT ME-100EA, molecular weight: 10000) and 7.8 mg of the aforementioned compounds (101) as dye were each weighted and dissolved in 8.0 mL of chloroform. To this solution, 7.3 mg of 4-dimethylaminopyridine (DMAP; Tokyo Chemical Industry Co., Ltd.) was added. To the solution obtained by adding DMAP, 2.8 mg of the water-soluble carbodiimide 1-ethyl-3-(3-dimethylaminopropyl)carbodiimide hydrochloride (which may be hereinafter abbreviated as WSC; Sigma Aldrich) was added.

The resultant solution was stirred at room temperature for 24 hours.

The resultant reaction solution was isolated and purified by dialysis using a dialysis membrane (Spectrum Laboratories, Inc., cutoff molecular weight: 3500) and methanol as a solvent.

From the recovered solution after the isolation and purification, the solvent was distilled off using an evaporator and the solution was dried using a vacuum drier to obtain the conjugate (A-1) of dye and polyethylene glycol.

Example B1

2.9 mg of conjugate (A-1) was dissolved in 2.0 mL of ultrapure water to prepare the conjugate solution (BA-1) As an additive, 3.2 mg of β-cyclodextrin (Tokyo Chemical Industry Co., Ltd.) was dissolved in 2.0 mL of ultrapure water to prepare the additive solution (BA-2).

The conjugate solution (BA-1) was added to the additive solution (BA-2) and the mixture was stirred at room temperature for 15 minutes to obtain the solution (BA-3). The solution (BA-3) was freeze-dried to obtain the composition (B-1).

Example B2

The composition (B-2) was obtained by a preparation process similar to Example B1 except that hydroxypropyl- β-cyclodextrin (Tokyo Chemical Industry Co., Ltd.) was used instead of β-cyclodextrin.

Comparative Example C1

The composition (C-1) was obtained by a preparation process similar to Example B1, except that β-cyclodextrin was not used.

Example D1

2.9 mg of the conjugate (A-1) was dissolved in 1.6 mL of chloroform to prepare the conjugate solution (DA-1).

As an additive, 3.2 mg of β-cyclodextrin was dissolved in 20 mL of ultrapure water to prepare the additive solution (DA-2)

The conjugate solution was dropped into the additive solution while stirring to prepare an emulsion preparation liquid.

The emulsion preparation liquid was exposed to ultrasound using an ultrasonic disrupter (Tomy, UD-200) at an intensity scale of 10 for 1 minute and 30 seconds to prepare an emulsion.

The emulsion was stirred with heating at 40° C. for 4 hours to remove chloroform in the emulsion. The recovered solution was filtered through a filter with 0.45 micrometer pore size to obtain the composition (D-1).

Example D2

The composition (D-2) was obtained in a preparation process similar to Example D1 except that hydroxypropyl-β-cyclodextrin was used instead of β-cyclodextrin.

Comparative Example E1

The composition (E-1) was obtained by a preparation process similar to Example D1, except that β-cyclodextrin was not used.

Example F1

738.4 mg of PEG having an amino group (NANOCS, PG1-AM-5k, molecular weight: 5000) and 312.0 mg of the aforementioned compounds (101) as dye were each weighted and dissolved in 20.0 mL of chloroform. To this solution 48.9 mg of 4-Dimethylaminopyridine (DMAP; Tokyo Chemical Industry Co., Ltd.) was added. To the solution obtained by adding DMAP, 76.7 mg of the water-soluble carbodiimide 1-ethyl-3-(3-dimethylaminopropyl) carbodiimide hydrochloride (which may be hereinafter abbreviated as WSC; Sigma Aldrich) was added.

The resultant solution was stirred at room temperature for 24 hours.

The resultant reaction solution was isolated and purified by dialysis using a dialysis membrane (Spectrum Laboratories, Inc., cutoff molecular weight: 2000) and methanol as a solvent.

From the recovered solution after the isolation and purification, the solvent was distilled off using an evaporator and the solution was dried using a vacuum drier to obtain the conjugate (F-1) of dye and polyethylene glycol.

Example F2

983.5 mg of PEG having an amino group (NANOCS, PG1-AM-2k, molecular weight: 2000) and 780.0 mg of the aforementioned compounds (101) as dye were each weighted and dissolved in 20.0 mL of chloroform. To this solution 122.2 mg of 4-Dimethylaminopyridine (DMAP; Tokyo Chemical Industry Co., Ltd.) was added. To the solution obtained by adding DMAP, 191.7 mg of the water-soluble carbodiimide 1-ethyl-3-(3-dimethylaminopropyl) carbodiimide hydrochloride (which may be hereinafter abbreviated as WSC; Sigma Aldrich) was added.

The resultant solution was stirred at room temperature for 24 hours.

The resultant reaction solution was isolated and purified by dialysis using a dialysis membrane (Spectrum Laboratories, Inc., cutoff molecular weight: 1000) and methanol as a solvent.

From the recovered solution after the isolation and purification, the solvent was distilled off using an evaporator and the solution was dried using a vacuum drier to obtain the conjugate (F-2) of dye and polyethylene glycol.

Example F3

100.0 mg of PEG having an amino group (NOF Corporation, SUNBRIGHT PTE-200PA, molecular weight: 20000) and 31.2 mg of the aforementioned compounds (101) as dye were each weighted and dissolved in 2.0 mL of chloroform. To this solution 4.9 mg of 4-Dimethylaminopyridine (DMAP; Tokyo Chemical Industry Co., Ltd.) was added. To the solution obtained by adding DMAP, 7.7 mg of the water-soluble carbodiimide 1-ethyl-3-(3-dimethylaminopropyl)carbodiimide hydrochloride (which may be hereinafter abbreviated as WSC; Sigma Aldrich) was added.

The resultant solution was stirred at room temperature for 24 hours.

The resultant reaction solution was isolated and purified by dialysis using a dialysis membrane (Spectrum Laboratories, Inc., cutoff molecular weight: 1000) and methanol as a solvent.

From the recovered solution after the isolation and purification, the solvent was distilled off using an evaporator and the solution was dried using a vacuum drier to obtain the conjugate (F-3) of dye and polyethylene glycol.

Example F4

50.1 mg of PEG having an amino group (NOF Corporation, SUNBRIGHT ME-050EA, molecular weight: 5000) and 59.2 mg of the aforementioned compounds (102) as dye were each weighted and dissolved in 4.0 mL of chloroform. To this solution 14.8 mg of 4-Dimethylaminopyridine (DMAP; Tokyo Chemical Industry Co., Ltd.) was added. To the solution obtained by adding DMAP, 22.8 mg of the water-soluble carbodiimide 1-ethyl-3-(3-dimethylaminopropyl)carbodiimide hydrochloride (which may be hereinafter abbreviated as WSC; Sigma Aldrich) was added.

The resultant solution was stirred at room temperature for 24 hours.

The resultant reaction solution was isolated and purified by dialysis using a dialysis membrane (Spectrum Laboratories, Inc., cutoff molecular weight: 2000) and methanol as a solvent.

From the recovered solution after the isolation and purification, the solvent was distilled off using an evaporator and the solution was dried using a vacuum drier to obtain the conjugate (F-4) of dye and polyethylene glycol.

Example G1

3.8 mg of the conjugate (F-1) was dissolved in 1.6 mL of chloroform to prepare the conjugate solution (GF-1).

As an additive, 180.0 mg of α-cyclodextrin was dissolved in 20 mL of ultrapure water to prepare the additive solution (GF-2).

The conjugate solution was dropped into the additive solution while stirring to prepare an emulsion preparation liquid.

The emulsion preparation liquid was exposed to ultrasound using an ultrasonic disrupter (Tomy, UD-200) at an intensity scale of 10 for 1 minute and 30 seconds to prepare an emulsion.

The emulsion was stirred with heating at 40° C. for 4 hours to remove chloroform in the emulsion.

The recovered solution was filtered through a filter with 0.45 micrometer pore size. This solution was freeze-dried to obtain the composition (G-1).

Example G2

The composition (G-2) was obtained in a preparation process similar to Example G1 except that β-cyclodextrin was used instead of α-cyclodextrin.

Example G3

The composition (G-3) was obtained in a preparation process similar to Example G1 except that hydroxypropyl-β-cyclodextrin was used instead of α-cyclodextrin.

Example G4

The composition (G-2) was obtained in a preparation process similar to Example G1 except that γ-cyclodextrin was used instead of α-cyclodextrin.

Comparative Example H1

The composition (H-1) was obtained by a preparation process similar to Example G1, except that α-cyclodextrin was not used.

Example L1

The composition (L-1) was obtained by a preparation process similar to Example G1, except that the conjugate (F-3) was used instead of the conjugate (F-1).

Example L2

The composition (L-2) was obtained in a preparation process similar to Example L1 except that β-cyclodextrin was used instead of α-cyclodextrin.

Example L3

The composition (L-3) was obtained in a preparation process similar to Example L1 except that hydroxypropyl-β-cyclodextrin was used instead of α-cyclodextrin.

Example L4

The composition (L-4) was obtained in a preparation process similar to Example L1 except that γ-cyclodextrin was used instead of α-cyclodextrin.

Comparative example M1

The composition (M-1) was obtained by a preparation process similar to Example L1, except that α-cyclodextrin was not used.

Example N1

The composition (N-1) was obtained by a preparation process similar to Example G1, except that the conjugate (F-4) was used instead of the conjugate (F-1).

Example N2

The composition (N-2) was obtained in a preparation process similar to Example N1 except that β-cyclodextrin was used instead of α-cyclodextrin.

Example N3

The composition (N-3) was obtained in a preparation process similar to Example N1 except that hydroxypropyl-β-cyclodextrin was used instead of α-cyclodextrin.

Example N4

The composition (N-4) was obtained in a preparation process similar to Example N1 except that γ-cyclodextrin was used instead of α-cyclodextrin.

Comparative Example P1

The composition (P-1) was obtained by a preparation process similar to Example N1, except that α-cyclodextrin was not used.

Example Q1

The composition (Q-1) was obtained by a preparation process similar to Example G1, except that the amount of α-cyclodextrin used was 360 mg.

Example Q2

The composition (Q-2) was obtained by a preparation process similar to Example G1, except that the amount of α-cyclodextrin used was 90 mg.

Example Q3

The composition (Q-3) was obtained by a preparation process similar to Example G1, except that the amount of α-cyclodextrin used was 45 mg.

Table 1 shows the results of measuring photoacoustic signal intensities (wavelength 780 nm) from the compositions (B-1), (B-2) and (C-1) obtained in the above Examples.

TABLE 1

| | Example B1 | Example B2 | Comparative Example C1 |
|---|---|---|---|
| Composition | B-1 | B-2 | C-1 |
| PA Signals per Unit Dye $(VJ^{-1}M^{-1})$ | $2.5 \times 10^6$ | $1.3 \times 10^6$ | $1.2 \times 10^6$ |

(Confirmation Accumulation in Tumor)

In the confirmation of accumulation in tumor, female outbred BALB/cSlc-nu/nu mice (6 weeks old at purchase; Japan SLC, Inc.) were used. For 1 week before injecting tumor cells, the mice were acclimated with a standard diet and bedding and in an environment allowing the mice to take diet and drink water ad libitum. Colon 26 (a mouse colon cancer cell) was injected hypodermically to the mice. By the time of experiment, the tumor was established in all the mice and the mice weighed 17 to 22 g. 100 µL (13 nmol of dye) each of the aforementioned compositions were intravenously injected at the tail into the mice bearing the tumors.

The mice receiving the composition were euthanized 24 hours after the administration and colon 26 tumors were extracted. The tumor tissues were transferred into plastic tubes, 1.25 volumes (in terms of tumor weight) of 1% aqueous solution of Triton-X100 was added, and the tissues were homogenized. Then, DMSO was added. Fluorescence intensities from the homogenates were measured with Odyssey® CLx Infrared Imaging System to quantified the dye in the tumor tissues.

Table 2 shows the results on tumor accumulation and blood concentrations of the compositions (B-1), (B-2), (C-1), (D-1), (D-2) and (E-1) obtained in the aforementioned Examples.

TABLE 2

|  | Example B1 | Example B2 | Comparative Example C1 | Example D1 | Example D2 | Comparative Example E1 |
|---|---|---|---|---|---|---|
| Composition | B-1 | B-2 | C-1 | D-1 | D-2 | E-1 |
| Tumor Accumulation (% ID/g) | 8 | 11 | 6 | 10 | 10 | 4 |
| Blood Concentration (% ID/g) | 2 | 2 | 3 | — | — | — |
| Ratio of Tumor Accumulation/Blood Concentration | 4 | 6 | 2 | — | — | — |

To the following compositions, 0.1 volumes (in terms of the volume of the solution before freeze-drying) of ultrapure water was added and the resultants were used for the confirmation experiments on tumor accumulation.

Table 3 shows the results on tumor accumulation and blood concentrations of the compositions (G-1), (G-2), (G-3), (G-4), (H-1) (L-1), (L-2), (L-3), (L-4), (M-1), (Q-1), (Q-2) and (Q-3) obtained in the aforementioned Examples.

TABLE 3

|  | Composition | Tumor Accumulation (% ID/g) | Blood Concentration (% ID/g) | Ratio of Tumor Accumulation/Blood Concentration |
|---|---|---|---|---|
| Example G1 | G-1 | 16.9 | 0.3 | 48.8 |
| Example G2 | G-2 | 12.5 | 0.6 | 32.1 |
| Example G3 | G-3 | 2.4 | 0.1 | 30.9 |
| Example G4 | G-4 | 2.3 | 0.1 | 47.2 |
| Example H1 | H-1 | 5.0 | 0.2 | 25.0 |
| Example L1 | L-1 | 9.6 | 4.2 | 2.3 |
| Example L2 | L-2 | 13.5 | 2.6 | 5.3 |
| Example L3 | L-3 | 12.8 | 5.4 | 2.4 |
| Example L4 | L-4 | 6.3 | 1.2 | 5.2 |
| Example M1 | M-1 | 0 | 0 | — |
| Example Q1 | Q-1 | — | — | — |
| Example G1 | G-1 | 16.9 | 0.3 | 48.8 |
| Example Q2 | Q-2 | 6.7 | 0.9 | 7.7 |
| Example Q3 | Q-3 | 2.3 | 0.1 | 16.3 |
| Example H1 | H-1 | 5.0 | 0.2 | 25.0 |

The composition prepared in (Example Q1) could not be dispersed when 0.1 volumes (in terms of the volume of the solution before freeze-drying) of ultrapure water was added.

Therefore, the compositions according to the Examples have excellent ratios of tumor accumulation to blood concentration and are excellent contrast agents that provide excellent visualization of tumor.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2014-181970, filed Sep. 8, 2014, and Japanese Patent Application No. 2015-172525, filed Sep. 2, 2015, which are hereby incorporated by reference herein in their entirety.

What is claimed is:

1. A contrast agent suitable for photoacoustic imaging, comprising: a compound represented by formula (1), (5), (6), or (7); and an additive, which interacts with the compound, wherein the additive is at least one selected from the group consisting of an α-cyclodextrin, a β-cyclodextrin, a hydroxypropyl-β-cyclodextrin, and a γ-cyclodextrin:

formula (1)

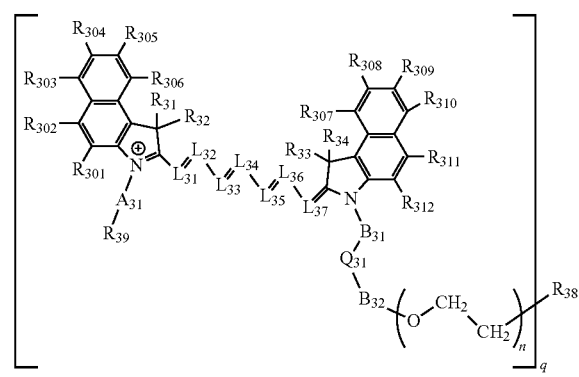

-continued formula (5)

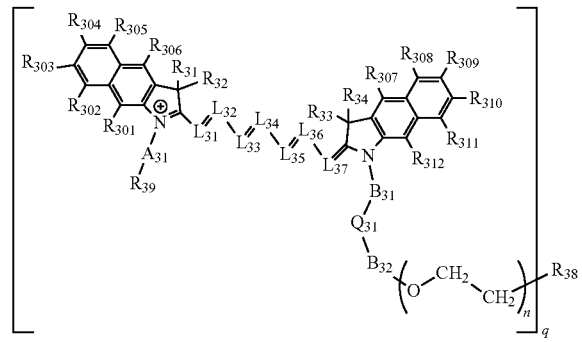

formula (6)

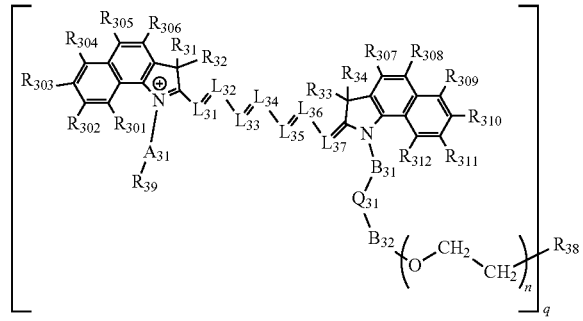

formula (7)

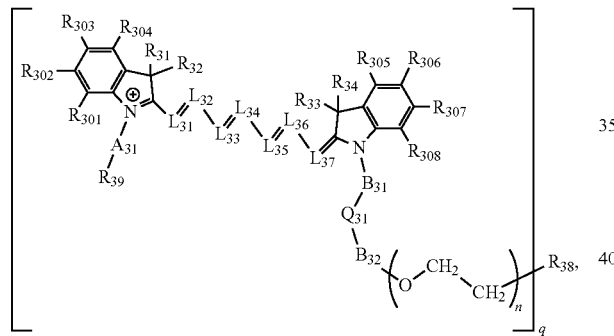

wherein $R_{301}$ to $R_{312}$ are each independently selected from the group consisting of a hydrogen atom, a halogen atom, $-PO_3T_{301}$, a substituted or unsubstituted phenyl group, thiophene group, or pyridinyl group and a linear or branched alkyl group having 1 to 18 carbon atoms;

$T_{301}$ is selected from the group consisting of a hydrogen atom, a sodium atom and a potassium atom;

$R_{31}$ to $R_{34}$ are each independently selected from the group consisting of a hydrogen atom and a linear or branched alkyl group having 1 to 18 carbon atoms;

$A_{31}$, $B_{31}$ and $B_{32}$ each independently represent a linear or branched alkylene group having 1 to 18 carbon atoms;

$L_{31}$ to $L_{37}$ are each independently selected from the group consisting of CH and $CR_{35}$ and may form a 4- to 6-membered ring;

$R_{35}$ is selected from the group consisting of a linear or branched alkyl group having 1 to 18 carbon atoms, a halogen atom, a substituted or unsubstituted phenyl group, pyridinyl group, or benzyl group, $ST_{302}$ and a linear or branched alkylene group having 1 to 18 carbon atoms;

$T_{302}$ is selected from the group consisting of a linear or branched alkyl group having 1 to 18 carbon atoms, a substituted or unsubstituted phenyl group and a linear or branched alkylene group having 1 to 18 carbon atoms;

$Q_{31}$ is selected from the group consisting of $-CONT_{31}$-, $-NT_{31}CO-$, $-NT_{31}(C=O) NT_{31}$-, $-NT_{31}(C=S) NT_{31}$-, $-NT_{31}(C=O)O-$, $-O-$, $-S-$, $-S(=O)_2NT_{31}$-, $-OP(=O)(OT_{31})O-$, $-S-S-$, $-CT_{31}=N-$, $-CT_{31}=N-NH-$, $-CT_{31}=N-O-$, $-CT_{31}=N-NH-O-$, $-CONT_{31}-R_{37}-(C=O)O-$, $-CONT_{31}-R_{37}-CONT_{31}$-, formula (2) and formula (3);

$T_{31}$ is selected from the group consisting of a hydrogen atom and an alkyl group having 1 to 5 carbon atoms;

$R_{37}$ is selected from the group consisting of $-CH(CO_2T_{37})$-, $-CH(CH_2CO_2T_{37})$- and a linear or branched alkylene group having 1 to 18 carbon atoms;

$T_{37}$ is selected from the group consisting of a hydrogen atom, a sodium atom, a potassium atom and an alkyl group having 1 to 5 carbon atoms;

$R_{38}$ is selected from the group consisting of an alkyl group having 1 to 18 carbon atoms, a hydrogen atom, $-OCH_3$, $-NH_2$, $-OH$, $-CO_2T_{38}$, $-S(=O)_2OT_{38}$, $-P(=O)(OT_{38})_2$ and $-OP(=O)(OT_{38})_2$;

$T_{38}$ is selected from the group consisting of a hydrogen atom, a sodium atom and a potassium atom;

$R_{39}$ is selected from the group consisting of a hydrogen atom, $-OCH_3$, $-NH_2$, $-OH$, $-S(=O)_2OT_{39}$, $-CO_2T_{39}$, $-P(=O)(OT_{39})_2$, $-CONH-CH(CO_2T_{39})$-$CH_2(C=O)OT_{39}$, $-CONH-CH(CO_2T_{39})$-$CH_2CH_2(C=O)OT_{39}$ and $-OP(=O)(OT_{39})_2$;

$T_{39}$ is selected from the group consisting of a hydrogen atom, a sodium atom and a potassium atom;

q is an integer from 1 to 20;

n is an integer from 2 to 250:

formula (2)

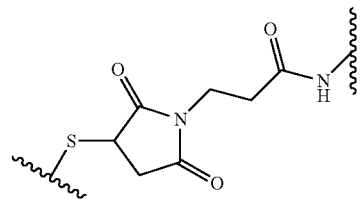

formula (3)

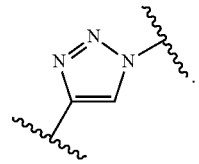

2. The contrast agent according to claim 1, wherein the compound represented by the formula (1), (5), (6), or (7) has a structure represented by Formula (501) or (601):

formula (501)
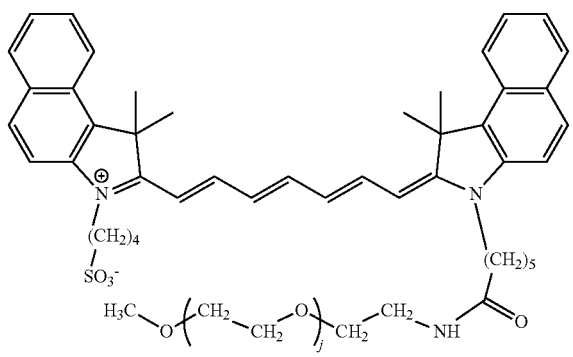
formula (601)
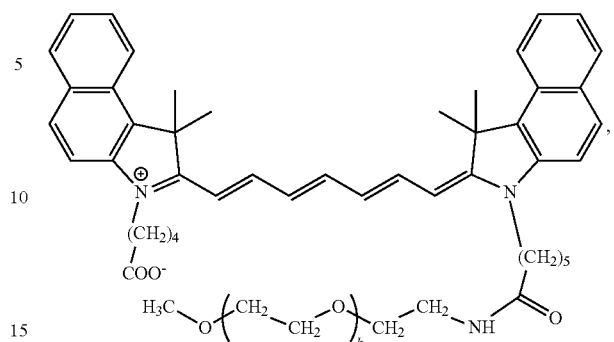
wherein j and k are each an integer from 2 to 250.
3. The contrast agent according to claim 1, wherein the compound has a molar extinction coefficient of $10^6$ $M^{-1}$ $cm^{-1}$ at a wavelength of 600 nm to 1300 nm.
4. The contrast agent according to claim 1, further comprising a dispersion medium.
* * * * *